US 7,435,426 B2

(12) United States Patent
Einziger et al.

(10) Patent No.: US 7,435,426 B2
(45) Date of Patent: Oct. 14, 2008

(54) MICRON SIZED BICARBONATE PARTICLES AND SLURRYS CONTAINING THE SAME

(75) Inventors: Mark D. Einziger, Manalapan, NJ (US); John Maziuk, Hightstown, NJ (US)

(73) Assignee: Church & Dwight Co., Inc., Princeton, NJ (US)

( * ) Notice: Subject to any disclaimer, the term of this patent is extended or adjusted under 35 U.S.C. 154(b) by 0 days.

(21) Appl. No.: 09/814,401

(22) Filed: Mar. 22, 2001

(65) Prior Publication Data

US 2002/0172713 A1 Nov. 21, 2002

(51) Int. Cl.
*A61K 47/00* (2006.01)
*A61K 6/00* (2006.01)
*A61K 9/68* (2006.01)
*A61K 9/14* (2006.01)
*A61K 8/00* (2006.01)
*A01N 25/00* (2006.01)
*A23K 1/165* (2006.01)

(52) U.S. Cl. ............... 424/439; 424/401; 424/405; 424/440; 424/442; 424/489; 424/49

(58) Field of Classification Search ............... 424/400, 424/49, 641, 717, 547, 439, 489
See application file for complete search history.

(56) References Cited

U.S. PATENT DOCUMENTS

| | | | | |
|---|---|---|---|---|
| 3,743,613 A | * | 7/1973 | Coulter et al. | 523/131 |
| 3,780,160 A | * | 12/1973 | Waggener et al. | 423/186 |
| 4,129,527 A | | 12/1978 | Clark et al. | 252/547 |
| 4,238,346 A | * | 12/1980 | Sugahara et al. | 510/471 |
| 4,414,130 A | * | 11/1983 | Cheng | 510/532 |
| 4,623,536 A | * | 11/1986 | Winston et al. | 424/49 |
| 5,071,558 A | * | 12/1991 | Itoh | 210/542 |
| 5,075,432 A | * | 12/1991 | Vanzo | 536/103 |
| 5,411,750 A | * | 5/1995 | Lajoie et al. | 424/717 |
| 5,424,077 A | | 6/1995 | Lajoie | 424/641 |
| 5,466,470 A | | 11/1995 | Lajoie | 424/641 |
| 5,518,727 A | | 5/1996 | Lajoie et al. | 424/400 |
| 5,645,840 A | | 7/1997 | Lajoie et al. | 424/400 |
| 5,855,871 A | * | 1/1999 | Masters et al. | 424/49 |
| 6,015,547 A | | 1/2000 | Yam | 424/49 |

* cited by examiner

*Primary Examiner*—Humera N Sheikh
(74) *Attorney, Agent, or Firm*—Allen R. Kipnes

(57) ABSTRACT

This invention provides substantially spherical, micron and submicron sized alkali metal bicarbonate particles. When combined with a liquid medium, the alkali metal bicarbonate particles have an exceptional capability to form a flowable slurry which demonstrates long term stability.

17 Claims, 1 Drawing Sheet

Church & Dwight Lot 6F025 sodium bicarbonate, 5% in KBr, Diffuse Reflectance, Bio Rad Win -IR. Res=4cm$^{-1}$ Church & Dwight Lot 6F025 sodium bicarbonate, 5% in KBr, Diffuse Reflectance, Bio Rad Win - IR, Res=4cm$^{-1}$

MICRON SIZED BICARBONATE PARTICLES AND SLURRYS CONTAINING THE SAME

BACKGROUND

It is known that the physicochemical properties of solids in particulate form are influenced by the size and shape of the particles. As particle size diminishes in scale, there is an enhancement of properties, and often the inception of new properties.

New commercial products are becoming available which provide special advantages because of fine particle size. Alkali metal bicarbonate, in particular, is a common reagent which has found application in a broad variety of products such as health care products, skin cleansers, skin care products, dentifrices, toothpolish, soft scrub cleansers, hard surface cleansers, agricultural products and the like.

There is evidence that fine particle size alkali metal bicarbonate can exhibit increased reactivity in comparison with coarse grain alkali metal bicarbonate. For example, in soda cracker production, finely divided sodium bicarbonate ingredient is more efficiently distributed and effectively reactive during the cracker dough preparation. The finished baked cracker is an improved product which has a substantially uniform texture, flavor and surface color, and a consistent pH throughout.

The coarse grain alkali metal bicarbonate particles of the prior art are often combined with liquid mediums to form slurrys. These prior art slurrys, however, are unstable and result in the formation of distinct layers of alkali metal bicarbonate particles and liquid medium after only a few minutes. These prior art slurrys, therefore, require the presence of a suspending aid which promotes stability in the otherwise unstable slurrys. The presence of a suspending aid, however, increases the cost of producing such slurrys. In addition, the presence of the suspending aid increases the likelihood of interaction between the components of the slurrys. In other utilities, the presence of a suspending aid is detrimental or prohibited by the end use of the product.

The solubility of prior art alkali metal bicarbonate particles falls off as temperature decreases. An alkali metal bicarbonate slurry, when combined with additional water to form a dilution, demonstrates decreased solubility of the alkali metal bicarbonate particles. This decreased solubility is apparent particularly at temperatures below 25° C. For example, a dilution made from a sodium bicarbonate slurry (the slurry being about 70% by weight of sodium bicarbonate particles, based upon 100% total weight of the slurry) and additional water at 22° C. will have 8.5% alkali metal bicarbonate particles dissolved therein. However, at 10° C., the dilution decreases to 7% alkali metal bicarbonate particles. Thus, time and fuel must be used to increase the temperature in order to facilitate the dissolution of the sodium bicarbonate particles. When such dilutions are used as dialyzates, both the cost and time of the medical treatment is increased.

Thus, there is continuing interest in the development of micron and submicron sized alkali metal bicarbonate particles, and slurrys containing the same, which exhibit a novel combination of properties, including increased stability and solubility, when utilized in health related, personal care, biologically active, household, and specialty type products.

Accordingly, it is an object of this invention to provide particulate alkali metal bicarbonate having a median particle size of from about 0.2 to about 50.0 μm with the particles having a surface area of from about 120 to about 140 $cm^3$ μg. The preferred range is from about 127 to about 130 $cm^3/g$.

It is another object of this invention to provide a stable, flowable slurry comprising alkali metal bicarbonate particles dispersed in a liquid medium, the particles remaining in suspension for an extended period of time without the requirement of a suspending aid.

It is another object of this invention to provide a stable, flowable slurry comprising alkali metal bicarbonate particles dispersed in a liquid medium, the particles having a median particle size of from about 0.2 to about 50.0 μm and a surface area of about 120 to about 140 $cm^3/g$. The slurry has a Zeta potential of from about 2 to about 11 mV and loose bulk density of about 1.40 to about 1.60 g/mL, and preferably about 1.49 g/mL.

It is another object of this invention to provide a stable, flowable slurry where the alkali metal bicarbonate particles are sodium bicarbonate particles having the particle size, surface area, Zeta potential and loose bulk density described above, as well as an IR spectra in the range of from about 4,000 $cm^{-1}$ to about 400 $cm^{-1}$, and preferably as shown in FIG. 1.

It is another object of this invention to provide an aqueous dilution containing alkali metal bicarbonate particles which may be prepared at a relatively low temperature and achieve a saturated solution in excess of non-invention materials.

Other objects and advantages of the present invention shall become apparent from the accompanying description and examples.

Publications of background interest with respect to the present invention subject matter include U.S. Pat. Nos. 5,411,750, 5,424,077, 5,466,470, 5,518,727 and 5,645,840, incorporated herein by reference in their entirety.

DESCRIPTION OF THE INVENTION

Figure 1:
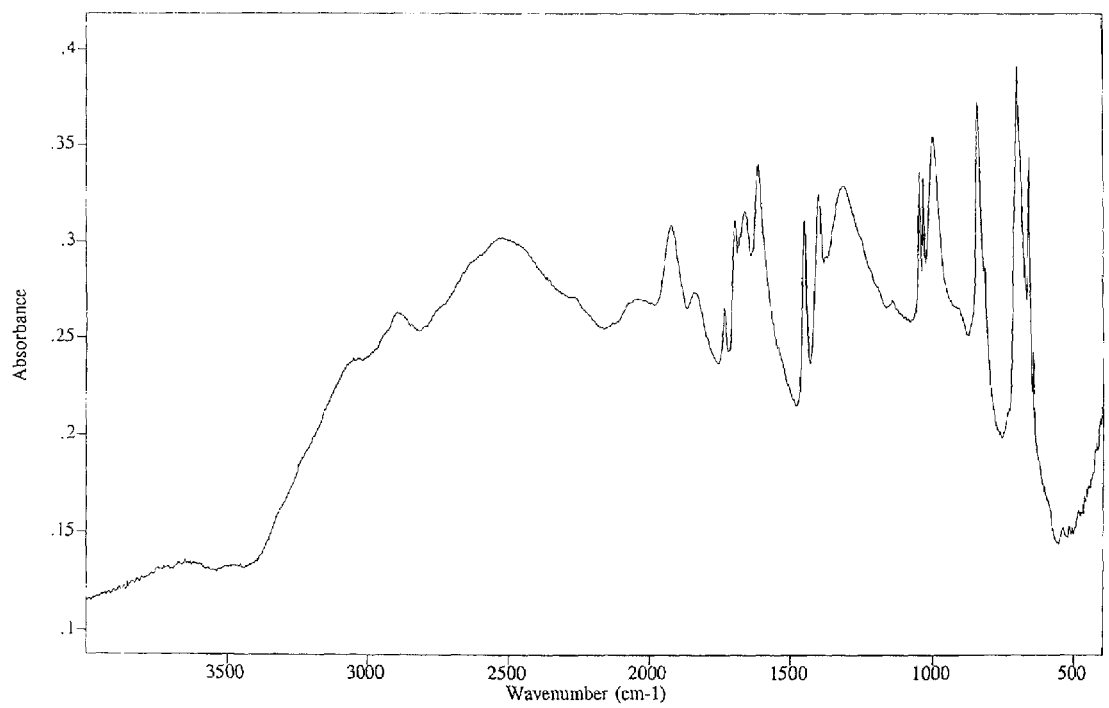
FIG. 1 shows the IR spectra of the alkali metal bicarbonate particles in the claimed slurry.

This invention provides substantially spherical, micron-sized and submicron-sized alkali metal bicarbonate particles having a median particle size of from about 0.2 to about 50.0 μm and the particles having a specific surface area of from about 120 to about 140 $cm^3/g$. The preferred range is from about 127 to about 130 $cm^3/g$.

In another embodiment, the invention provides a stable, flowable slurry comprising, preferably consisting essentially of, and more preferably consisting of, alkali metal bicarbonate particles dispersed in a liquid medium where the alkali metal bicarbonate particles have a median particle size of from about 0.2 to 50.0 μm and a surface area of from about 120 to about 140 $cm^3/g$ and preferably from about 127 to about 130 $cm^3/g$. The slurry has a loose bulk density of from about 1.40 to about 1.60 grams/mL, and preferably about 1.49 grams/mL, and a Zeta potential of about 2 to about 11 mV. The slurrys of the present invention are stable for months and do not require the presence of a suspending aid.

In another embodiment, this invention provides a stable, flowable slurry comprising, preferably consisting essentially of, and more preferably consisting of, sodium bicarbonate particles with the above parameters and an IR spectra of from about 4,000 $cm^{-1}$ to about 400 $cm^{-1}$.

In another embodiment, the dilution of the present invention achieves rapid dissolution of the alkali metal bicarbonate slurry at low temperatures, typically 5° to 20° C., preferably 10° to about 20° C., in substantially the same concentration as that attained at room temperature (generally about 22.5° C.).

The dilution of the present invention demonstrates a saturation concentration of about 8.5% of sodium bicarbonate at room temperature and about 8.5% of sodium bicarbonate at 10° C. Saturation with potassium bicarbonate at 10° C. with the present invention is approximately the same as saturation of potassium bicarbonate at room temperature. Thus, present invention dilutions may be utilized at lower temperatures making them more economical, convenient and efficient than prior art dilutions.

In another embodiment, the dilution of the present invention is made from a sodium bicarbonate slurry and used as a dialyzate.

The term "median particle size" as employed herein refers to a point where in a given sample approximately 50% of the particles are smaller in size and 50% of the particles are larger in size.

The procedure employed to prepare the substantially spherical, micron-sized particles of alkali metal bicarbonate and the slurry follows. The particle shape and particle size results directly from this particular method of preparation. Present invention alkali metal bicarbonate particles have a median particle size of from about 0.2 to about 50.0 microns.

An important aspect of the current invention is the use of a horizontal bead mill for the wet milling step in the preparation of the invention particles and slurrys.

The particles and slurry of this invention are prepared by pre-blending a sterilized water source with Church & Dwight grade 1.5 or 4 alkali metal bicarbonate particles having an average particle size of from about 175 μm to about 45 μm. This mixture forms the initial charge which is then placed into a running wet media processing mill. The charge is then processed in the mill for about eight to about 18 minutes at about 3,000 to about 4,500 rotations per minute. Preferably, the charge is processed for about 15 minutes. Preferably, the charge is processed at about 3,200 rotations per minute. The contents of the mill is then emptied.

In the process of preparing the slurry, the wet milling may occur in the presence of an inert grinding medium, such as Yttrium stabilized zirconia beads, stainless steal beads, among other known in the art. Preferably, this inert media is 0.4 mm Yttrium stabilized zirconia-grinding beads.

The resulting slurry contains from about 50% to about 80% by weight of alkali metal bicarbonate, based on 100% total weight of the slurry. Preferably, the alkali metal bicarbonate in the slurry is present in a range from about 60% to about 75% by weight, based on 100% total weight of the slurry. Most preferably, the alkali metal bicarbonate present in the initial charge is about 70% by weight, based on 100% total weight of the slurry.

The alkali metal bicarbonate particles contained within the slurry have a median particle size of from about 0.2 μm to about 50.0 μm. Not more than about 0.1% of the particles in the slurry exceed 50.0 μm. Preferably, the alkali metal bicarbonate particles in the slurry have a particle size of 0.2 μm to 25 μm, preferably 0.2 μm to 15 μm, still more preferably the particles in the slurry do not exceed 1 μm. Most preferably, the alkali metal bicarbonate particle size is from about 0.4 μm to about 0.7 μm.

The alkali metal bicarbonate particles of this invention may be sodium bicarbonate particles or potassium bicarbonate particles.

The resulting alkali metal bicarbonate particles in the slurry have a specific surface area of from about 120 to about 140 cm$^3$/g, and preferably from about 127 to about 130 cm$^3$/g in a slurry comprising 50 to 80%, preferably 60 to 75%, more preferably 65 to 72%, and most preferably about 70%, by weight of alkali metal bicarbonate, and 20 to 50%, preferably 20 to 40%, more preferably 28 to 35% and most preferably about 30%, by weight of a liquid medium, based on 100% total weight of the slurry.

The Zeta potential of the resulting slurry is 2 to 11 mV when an aliquot of the slurry is dissolved in isopropyl alcohol in standard means known in the art. The bulk density of the slurry is from about 1.40 to 1.60 grams/mL and preferably 1.49 grams/mL.

The viscosity of the slurry of the present invention is less than about 1,000 cP. The procedure for measuring viscosity is described below.

An aqueous dilution comprising sodium bicarbonate of this invention may be prepared by wet-milling the particles as described above where the resulting slurry is combined with water resulting in a dilution having from about 10.00 to about 11.43% by weight of the sodium bicarbonate slurry, based on 100% total weight of the aqueous dilution, and from about 88.57 to about 90.00% by weight of additional water, based on 100% total weight of the dilution.

The dilution may be used as a dialyzate in dialysis treatment.

The slurry may be contained within a dialysis treatment dispenser to which additional water is added to form a dialyzate. Such a dispenser may be made of a material such as plastic, glass, foil or cardboard.

Present invention micron sized alkali metal bicarbonate particles, and the slurrys and dilutions containing these particles, exhibit a novel combination of properties when utilized as ingredients in health care, personal care and specialty type products.

Present invention slurrys demonstrate excellent flowability and high stability.

Present invention dilutions containing sodium bicarbonate particles provide an improved dialyzate.

Present invention dilutions demonstrate the ability to attain a concentration of sodium bicarbonate particles in solution at low temperatures which would not be achieved with larger particles.

Present invention alkali metal bicarbonate particles and slurrys enhance odor absorption and neutralization in personal care products, such as those adapted for skin care and oral care.

Present invention alkali metal bicarbonate particles and slurrys provide improved esthetics in creams, lotions, gels, ointments, soapbars, toothpastes, deodorants and the like. Irritation is minimized, skin mildness is improved, and anti-bacterial/antifungal activity is increased.

Present invention alkali metal bicarbonate particles and slurrys provide improved consistency in antacids.

Present invention alkali metal bicarbonate particles and slurrys provide improved cleaning capabilities in household cleaners.

Present invention alkali metal bicarbonate particles and slurrys may be combined with adjuvants, such as fragrances, colorants, surfactants, suspending agents, buffers, abrasives, antioxidants, bacteriocides, fungicides, antiseptics, astringents, humectants, tartar control agents, anticorrosives and mixtures thereof, to form the products described above.

Present invention alkali metal bicarbonate particles and slurrys may be combined with carriers, such as alcohols, glycols and mixtures thereof, to form the products described above.

Standard procedures are followed for measurement of the physical properties of the particles, slurrys and dilutions of the present invention.

Particle size is determined by using a Pacific Scientific Instruments, Model 8000A/3000A/MC05 analyzer.

Specific surface area is determined by using the Beckman Coulter LS230 Particle Size Analyzer.

Loose bulk density is determined by using the Hosokawa Micron Corporation Powder Tester.

Zeta potential is determined by using the Beckman Coulter Delsa 440SX Zeta Potential/Electrophoretic Mobility Analyzer.

Viscosity of the slurry is determined by using a Brookfield Visometer RVT unit operated at 50 rpm with a No. 2 spindle at about 22° C.

The following examples are further illustrative of the present invention. The components and specific ingredients are presented as being typical, and various modifications can be derived in view of the forgoing disclosure within the scope of the invention.

EXAMPLES

Example 1

Example 1 illustrates the preparation of the micron-sized particles by a wet mill process of the present invention and the resulting stable, flowable slurry.

The preparation of Example 1 involves a wet mill process. In this process, a sterilized water source is pre-blended with either Church & Dwight grade 1.5 or grade 4 sodium bicarbonate. Church & Dwight grade 1.5 sodium bicarbonate has a median particle size of about 85 to about 100 μm. Church & Dwight grade 4 sodium bicarbonate has a median particle size of about 150 μm. Table 1 sets forth their parameters.

TABLE 1

| Church & Dwight Grade | Sieve Size (Tyler U.S. Mesh) | Minimum Particles Remaining on Sieve | Maximum Particles Remaining on Sieve |
|---|---|---|---|
| 1.5 | 100 | 0% | 0.9% |
| 1.5 | 200 | 20% | 45% |
| 1.5 | 325 | 80% | 100% |
| 4 | 80 | 0% | Trace |
| 4 | 100 | 0% | 2% |
| 4 | 200 | 80% | 100% |
| 4 | 325 | 93% | 100% |

The mixture is placed into a running Eiger self-contained horizontal feed mill. The media utilized is 45% by weight of 0.4 mm Yttrium stabilized zirconia grinding beads. The bicarbonate charge is 70% and the water charge is 30%, by weight of the total charge. The process is conducted at a temperature of about 10° C. The wet-milling occurs for a time of fifteen minutes at a speed of about 3,200 rotations per minute. After the ingredients are processed for fifteen minutes, the resulting slurry is emptied from the bead mill.

The resulting slurry initially has a flowable consistency. After thirty minutes, the resulting slurry maintains a flowable consistency. The resulting bicarbonate particles contained in the slurry have a median size of about 0.4 μm to about 0.7 μm. The results are shown on Table 2, Example 1.

Comparative Example A is prepared using a dry mill process and Comparative Examples B-D are prepared using air milled particles. The sterilized water is pre-blended with the sodium bicarbonate particles.

As can be seen from Table 2, the initial consistency of Comparative Example A is not a slurry; the sodium bicarbonate settled out within two minutes. The initial consistency of Comparative Examples B-D is that of wet cement. After 30 minutes, the consistency of Comparative Examples B-D becomes hard packed.

TABLE 2

| Example | Median Particle Size | Consistency | Consistency after 30 Minutes |
|---|---|---|---|
| Example 1 | 0.4-0.7 μm | Flowable slurry | Flowable |
| Comparative Example A | greater then 15 μm | no slurry; sodium bicarbonate settled out within 2 min. | N/A |
| Comparative Example B | 15 μm | wet cement | hard packed |
| Comparative Example C | 10 μm | wet cement | hard packed |
| Comparative Example D | 5 μm | wet cement | hard packed |
| Comparative Example E | — | paste | N/A |
| Comparative Example F | — | hard packed | N/A |

Comparative Example E was prepared according to the process used Example 1, except that a ball mill was used, rather than a horizontal bead mill. The milling time was greater than 72 hours with losses greater than 50%. As can be seen on Table 2, the initial resulting material has a paste-like consistency.

Comparative Example F was prepared according to method used to prepare Example 1 using Church & Dwight grade 1.5 particles and also included homogenization. The initial resulting material was hard packed, as can be seen on Table 2.

Example 2

Example 2 illustrates the preparation of an oral care product, specifically a toothpaste, gel or polish.

In these applications, the alkali metal bicarbonate slurry is present from about 1.43 to about 98%.

Humectants are also present in these formulations in amounts of from about 5 to about 50%, preferably about 10 to about 40%. Exemplary humectants include, but are not limited to glycerin, sorbitol, mannitol, etc.

These formulations may also contain abrasives in addition to any solid alkali metal bicarbonate which may be present. When present such abrasives can comprise up to about 50% of the formulation. Exemplary, non-limiting abrasives include silica, aluminum oxide, talc, calcium carbonate, etc. When calcium carbonate is used, it should not be calculated as part of the bicarbonate ion source as calcium carbonate has very low solubility and does not practically contribute any significant amount of carbonate ion to the solution.

Surfactants may also be present in amounts of from about 0.1 to about 10%, preferably about 0.3 to about 3% of the formulation, and may be selected from anionic, nonionic, and amphoteric surfactants. Typical surfactants include, but are not limited to sodium lauryl sulfate.

Foam boosters, where desired may also be present in amounts of up to about 2% of the formulation. A typical non-limiting example foam booster is sodium lauroyl sarcosinate.

A further optional ingredient in these formulations is a thickener or viscosity enhancer. When present, this component comprises up to about 15% of the formulation. Typical, non-limiting examples include carboxymethylcellulose (or its sodium salt), magnesium aluminum silicate, carrageenan gum, fumed silica, and hydrated silica.

Other typical ingredients in a formulation of this type include, but are not limited to a cavity control agent (such as sodium fluoride, monoflurophosphate, etc.), a tartar control agent (such as tetrasodium pyrophosphate, etc.), sensitivity reduction agents (such as potassium nitrate, etc.), sweeteners (such as sodium saccharine, ace-K, aspartame, sucralose, etc.), flavors and dyes.

Example 3

Example 3 illustrates the preparation of a skin cleanser.

For use in this application, the solution should preferably have alkali metal bicarbonate slurry in an amount of at least 1.43%.

These formulations usually contain from about 5% to about 30% surfactants. The surfactants of choice include, but are not limited to, sodium alphaolefin sulfonates, cocamidopropyl betaines, and alkylbenzene sulfonates.

Lathering agents or foam boosters are often present and when present comprise up to 5% of the formulation. Examples include, but are not limited to, anionic or amphoteric surfactants. Preferred surfactants include, but are not limited to, lauramnide MEA, sodium lauroylsarcosinate, and sodium cocoylisothionate.

Thickeners or viscosity enhancers may also be present up to about 10% of the formulation. Examples include, but are not limited to, carboxymethylcellulose, hydroxypropylcellulose, hydroxyethylcellulose, hydroxypropyl guar gum, magnesium aluminum silicate, and carrageenan gum.

Other optional ingredients typical to skin cleanser formulations include, but are not limited to, antimicrobial agents, preservatives, skin substantive aids, chelating agents, fragrances, dyes, etc. A particularly preferred antimicrobial is Triclosan, while a particularly preferred preservative is sodium hydroxymethylglycinate or methylparaben. A preferred chelating agent is EDTA or its salts.

Example 4

Example 4 illustrates the preparation of an ostomy deodorant.

In this application, alkali metal bicarbonate slurry is typically present in amounts of from about 1.43% to up to about 35.75% of the formulation. A zinc source concentration in an amount to yield a zinc ion concentration about 0.01 to about 2 wt % of the formulation. Stabilizing anion concentration is set at the minimums as discussed in the examples above. In addition, the formulations can have solvents such as alcohols, preferably ethyl alcohol, preservatives, fragrances, and dyes, as may be desired. Typical examples include, but are not limited to, those mentioned in the foregoing examples.

As an alternative, the formulation can be provided as a pre-mixed powder for reconstitution before adding to the ostomy bag.

Example 5

Example 5 illustrates the preparation of a toilet deodorizer/sanitizer.

Products of this nature include solutions which dispense into the toilet tank with each flush as well as solid products which are placed in the toilet tank and dissolve slowly over time. In either case, zinc ion source compounds and alkali metal bicarbonate compounds can be added to the solution for dispensing or incorporated as dry components in the solid products. The liquid products should adhere to the limitations above for a clear solution so that there will be proper dispensing of usable zinc ion and usable bicarbonate. The solid product need only be limited to having sufficient amounts so that the water standing in the toilet tank awaiting the next flush adheres to the clear solution limitations above. The other components of such products are well known in the art.

Example 6

Example 6 illustrates the preparation of a hard surface cleaner.

In these applications, the alkali metal bicarbonate slurry is present from about 714 parts by weight per 1,000 parts of the suspension.

Three suspension components including an amine oxide surfactant, a multiple ionic-oxide containing salt and as alkylaryl sulfonate salt are included in the suspension. The amine oxide surfactant is present from about 12 parts by weight per 1,000 parts of the suspension to about 40 parts by weight per 1,000 parts of the suspension. The multiple ionic-oxide containing salt is present from about 2 parts by weight per 1,000 parts of the suspension to about 30 parts by weight per 1,000 parts of the suspension. The alkylaryl sulfonate salt is present in at least about 16.5 parts by weight per 1,000 parts of the suspension.

Coloring agents and perfumes may also be added to the suspension.

We claim:

1. A slurry comprising from about 50 to about 80% by weight of substantially spherical alkali metal bicarbonate particles, said particles having a median particle size of from about 0.2 to about 50.0 µm and a surface area of from about 120 to about 140 cm$^3$/g, dispersed in a liquid medium, wherein the slurry has a viscosity of less than about 1,000 cP and a Zeta potential of about 2 to about 11 mV, wherein the slurry is stable and is prepared in the absence of a suspending aid.

2. The slurry of claim 1, wherein the alkali metal bicarbonate particles have a median particle size of from about 0.2 to about 25.0 µm.

3. The slurry of claim 2, wherein the alkali metal bicarbonate particles have a median particle size of from about 0.5 to about 1.0 µm.

4. The slurry of claim 3, wherein the slurry comprises from about 60 to 75% by weight of alkali metal bicarbonate and from about 20% to about 40% by weight of liquid medium, based upon 100% total weight of the slurry.

5. The slurry of claim 1, wherein the slurry comprises from about 60 to about 75% by weight of alkali metal bicarbonate and from about 25 to about 40% by weight of liquid medium, based upon 100% total weight of the slurry.

6. The slurry of claim 5, wherein the slurry comprises from about 65 to about 72% by weight of alkali metal bicarbonate and from about 28 to about 40% by weight of liquid medium, based upon 100% total weight of the slurry.

7. The slurry of claim 6, wherein the slurry comprises about 70% by weight of alkali metal bicarbonate and about 30% by weight of liquid medium, based upon 100% total weight of the slurry.

8. The slurry of claim 1, wherein the liquid medium is water.

9. The slurry of claim 3, wherein the alkali metal bicarbonate particles are sodium bicarbonate particles.

10. The slurry of claim 1, wherein the alkali metal bicarbonate particles have an IR spectra as shown in FIG. 1.

11. A method of using the slurry of claim 1 comprising (1) incorporating said slurry with materials to form a bicarbonate containing product selected from the group consisting of a dialyzate, a toothpaste, a personal cleanser, a chewing gum, an antacid, a mouthwash, a deodorant, a detergent, a skin care product, a household cleanser, an industrial cleaner, a blasting medium, an animal feed product, a baking product and a pesticidal product by dissolving from about 10.00 to about 12.00% by weight of the slurry in about 88 to 92% by weight of additional water, based upon 100% total weight of the slurry and said additional water to form an aqueous dilution, and (2) further incorporating said materials.

12. The method of claim 11, wherein said bicarbonate containing product is a dialyzate.

13. The method of claim 11, wherein said slurry is diluted.

14. A product comprising the slurry of claim 1, wherein the product is selected from the group consisting of a dialyzate, a toothpaste, a personal cleanser, a chewing gum, an antacid, a mouthwash, a deodorant, a detergent, a skin care product, a household cleanser, an industrial cleaner, a blasting medium, an animal feed product, a baking product and a pesticidal product.

15. The product of claim 14, further comprising an adjuvant selected from the group consisting of fragrances, colorants, surfactants, buffers, abrasives, antioxidants, anticorrosives, bacteriocides, fungicides, antiseptics, astringents, humectants, tartar control agents, and mixtures thereof.

16. The product of claim 14, wherein the liquid medium is selected from the group consisting of water, alcohols, glycols, and mixtures thereof.

17. The slurry of claim 1 having a density of about 1.40 to about 1.60 g/mL.

* * * * *